United States Patent
Iwashita et al.

(10) Patent No.: US 10,787,473 B2
(45) Date of Patent: Sep. 29, 2020

(54) PH RESPONSIVE FLUORESCENT COMPOUND, COMPOSITION FOR DETECTING MITOPHAGY USING SAME, AND METHOD FOR DETECTING MITOPHAGY WITHIN CELLS

(71) Applicant: DOJINDO LABORATORIES, Kamimashiki-gun, Kumamoto (JP)

(72) Inventors: Hidefumi Iwashita, Kumamoto (JP); Ryo Sakamoto, Kumamoto (JP); Munetaka Ishiyama, Kumamoto (JP)

(73) Assignee: DOJINDO LABORATORIES, Kamimashiki-Gun, Kumamoto (JP)

( * ) Notice: Subject to any disclaimer, the term of this patent is extended or adjusted under 35 U.S.C. 154(b) by 0 days.

(21) Appl. No.: 16/078,299

(22) PCT Filed: Feb. 23, 2017

(86) PCT No.: PCT/JP2017/006824
§ 371 (c)(1),
(2) Date: Aug. 21, 2018

(87) PCT Pub. No.: WO2017/146145
PCT Pub. Date: Aug. 31, 2017

(65) Prior Publication Data
US 2019/0062356 A1 Feb. 28, 2019

(30) Foreign Application Priority Data

Feb. 26, 2016 (JP) .................... 2016-036474

(51) Int. Cl.
| | | |
|---|---|---|
| C07F 9/59 | (2006.01) | |
| G01N 33/52 | (2006.01) | |
| C07F 9/6558 | (2006.01) | |
| G01N 21/64 | (2006.01) | |
| G01N 21/77 | (2006.01) | |
| G01N 33/58 | (2006.01) | |
| C09K 11/06 | (2006.01) | |
| G01N 33/50 | (2006.01) | |

(52) U.S. Cl.
CPC .......... *C07F 9/65583* (2013.01); *C09K 11/06* (2013.01); *G01N 21/64* (2013.01); *G01N 21/77* (2013.01); *G01N 33/5079* (2013.01); *G01N 33/52* (2013.01); *G01N 33/582* (2013.01); *G01N 2800/2835* (2013.01)

(58) Field of Classification Search
CPC .................................................. C07F 9/65583
See application file for complete search history.

(56) References Cited

U.S. PATENT DOCUMENTS

2012/0126175 A1  5/2012  Ueno

FOREIGN PATENT DOCUMENTS

| EP | 0 810 291 A1 | 12/1997 |
| JP | 2003-508466 A | 3/2003 |
| WO | 1996/025518 A1 | 8/1996 |
| WO | 2001/017356 A1 | 3/2001 |
| WO | 2010/055789 A1 | 5/2010 |

OTHER PUBLICATIONS

Iwashita et al. ACS Chem. Biol. 2017, 12, 2546-2551 (Year: 2017).*
Liming Huang and Suk-Wah Tam-Chang, "9-Piperazine substituted perylene-3,4-dicarboximide as a fluorescent probe in ratiometric analysis," Chemical Communications, vol. 47, pp. 2291-2293 (2011), The Royal Society of Chemistry.
Takako Kogure et al., "A fluorescent variant of a protein from the stony coral Montipora facilitates dual-color single-laser fluorescence cross-correlation spectroscopy," Nature Biotechnology, vol. 24, No. 5, pp. 577-581 (May 2006), Springer Nature.
Min Hee Lee et al., "Mitochondria-Immobilized pH-Sensitive Off—on Fluorescent Probe," Journal of the American Chemical Society, vol. 136, pp. 14136-14142 (2014), ACS Publications.
China National Intellectual Property Administration, "Notification of First Office Action", issued in Chinese Patent Application No. 201780012747.0, which is a counterpart to U.S. Appl. No. 16/078,299, dated Jan. 2, 2020, 11 pages (5 pages of English translation of Office Action and 6 pages of original Office Action).

* cited by examiner

*Primary Examiner* — Emily A Bernhardt

(57) ABSTRACT

Disclosed is a pH-responsive fluorescent compound, represented by the general formula, which is a novel pH-responsive fluorescent compound capable of being specifically localized in mitochondria within cells, which exhibits strong fluorescence under weakly acidic pH environments in lysosomes, and which is not readily subject to interference from autofluorescence and background fluorescence due to other fluorescent substances within cells. Also disclosed are a composition for detecting mitophagy using the pH-responsive fluorescent compound, and a method for detecting mitophagy within cells.

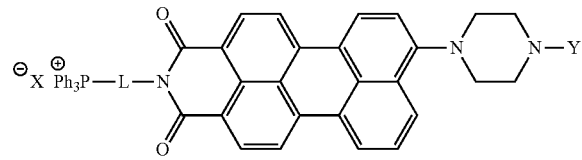

In the general formula, L represents a linker, X represents a pharmaceutically acceptable anion, and Y represents a reactive group that may react with a functional group on a mitochondrial protein to form a covalent bond.

3 Claims, 5 Drawing Sheets

PH RESPONSIVE FLUORESCENT COMPOUND, COMPOSITION FOR DETECTING MITOPHAGY USING SAME, AND METHOD FOR DETECTING MITOPHAGY WITHIN CELLS

TECHNICAL FIELD

The present disclosure relates to a novel pH responsive fluorescent compound, a composition for detecting mitophagy using the same and a method for detecting mitophagy within cells.

BACKGROUND ART

In cells, there is a cellular process for disassembling unnecessary proteins and organelle in cells, which is called autophagy. In this process, the unnecessary proteins and organelle are enveloped by a phagophore consisting of a lipid bilayer membrane called autophagosome and decomposed after a fusion with lysosome. A selective decomposition/removal process of mitochondria through the autophagy is called mitophagy, which is considered to play a role in protecting an organism from a disease in which a dysfunction of the mitochondria involves.

A general method for detecting the mitophagy includes a method in which an expression of a mitophagy associated factor in mRNA obtained from a cell lysate by means of Western Blot. That method is not applicable for a live cell imaging because the cells are lysed.

A typical intracellular imaging method includes a method in which an intensity of fluorescence from a pH responsive fluorescent protein called Keima expressed in the mitochondria (for example, see Non-Patent Literature 1) is monitored. The excitation spectrum of Keima changes responding to pH: a short wavelength (440 nm) peak is predominant in a neutral environment, whereas a long wavelength (550 nm) peak is predominant in an acidic environment. In a ratio (550 nm/440 nm) image obtained from two images obtained using these two different excitation wavelength, Keima in the neutral environment shows lower ratio value, whereas Keima in the acidic environment shows higher ratio value. Using this phenomenon, mitophagy may be detected by reading out the pH change around the mitochondria associated with mitophagy from the fluorescence image. However, this method is not applicable to all kinds of cells because the expression of Keima in the cells is required.

Under these circumstances, a compound represented by a formula shown below has been proposed as a pH responsive fluorescent dye which may be introduced in cells through cellular membrane, may be localized to the mitochondria specifically, of which emission intensity changes responding to the pH change of the mitochondria (see Non-Patent Literature 2). This compound has a triphenyl phosphonium group for specifically localizing into the mitochondria; a piperazine ring having a pH sensor functionality; a chloromethyl group, a reactive group that may form a covalent bond with mitochondrial protein and a naphtahleneimide group, a fluorescent chromophore in one molecule.

[Chemical Formula 1]

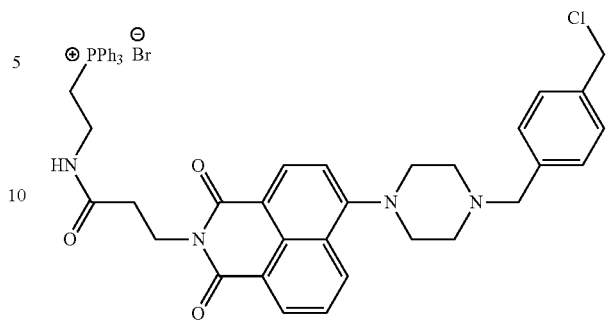

CITATION LIST

Non-Patent Literature

Non-Patent Literature 1: Kogure, T., Karasawa, S., Araki, T., Saito, K., Kinjo, M., and Miyawaki, A., A fluorescent variant of a protein from the stony coral Montipora facilitates dual-color single-laser fluorescence cross-correlation spectroscopy; *Nature Biotechnology.* 24:577-581 (2006).

Non-Patent Literature 2: Mitochondria-Immobilized pH-Sensitive Off-On Fluorescent Probe, Min Hee Lee, Nayoung Park, Chunsik Yi, Ji Hye Han, Ji Hye Hong, Kwang Pyo Kim, Dong Hoon Kang, Jonathan L. Sessler, Chulhun Kang, and Jong Seung Kim, *J. Am. Chem. Soc.* 2014, 136, 14136-14142.

SUMMARY OF INVENTION

Technical Problem

However, the pH responsive fluorescent compound as described in Non-Patent Literature 2 having naphtahleneimide as the fluorescent chromophore has a maximum excitation wavelength of about 440 nm, of which emission intensity is low when excited with a 488 nm laser (B excitation) of a commonly used fluorescence microscope. In addition, a background emission is high because endogenous fluorescent substances in the cells are also excited, which causes a problem of low detection sensitivity of the mitophagy. Increasing the concentration of the pH responsive fluorescent compound to solve the problem of low sensitivity may increase a damage on the mitochondria. Consequently, the pH responsive fluorescent compound for detecting the mitophagy may induce the mitophagy, which hamper the precise detection of the mitophagy. Hence, it is desirable that the pH responsive fluorescent compound showing high fluorescent intensity when excited at B excitation or G excitation (546 nm) is used in a concentration as low as possible.

The present disclosure is achieved under such circumstances and the object of the present disclosure is to provide a novel pH responsive fluorescent compound that may be localized to the mitochondria in the cells specifically, emits strong fluorescence in a slight acidic environment in the lysosomes and hardly affected by autofluorescence or background emission arised from other fluorescent substances in the cells, a composition for detecting the mitophagy using the same and a method for detecting the mitophagy within cells.

Solution to Problem

First aspect of the present disclosure according to the object as mentioned above provides a pH responsive fluorescent compound represented by a general formula shown below to solve the problem as mentioned above.

[Chemical Formula 2]

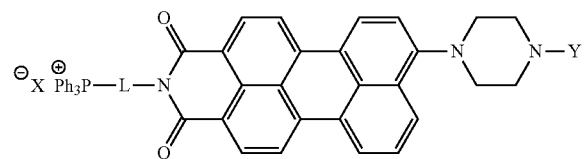

In the general formula as shown above,
L represents a linker;
X represents a pharmaceutically acceptable anion; and
Y represents a reactive group that may react with a functional group on a mitochondrial protein to form a covalent bond.

Second aspect of the present disclosure provides a composition for detecting mitophagy containing the pH responsive fluorescent compound represented by a general formula shown above to solve the problem as mentioned above.

Third aspect of the present disclosure provides a method for detecting mitophagy comprising a step for administering the pH responsive fluorescent compound represented by a general formula shown above into cells and a step for measuring a fluorescent emission from the cells after incubating for certain period to solve the problem as mentioned above.

In the first to third aspects of the present disclosure, the pH responsive fluorescent compound may be the compound represented by Formula 9 as shown below.

[Chemical Formula 3]

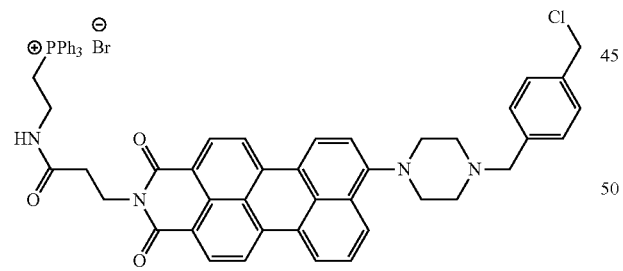

Advantageous Effects of Invention

The pH responsive fluorescent compound represented by the general formula shown above has a triphenyl phosphonium group for specifically localizing into the mitochondria; a piperazine ring having a pH sensor functionality; a reactive group that may form a covalent bond with mitochondrial protein and a perylene imide group, a fluorescent chromophore in one molecule. Therefore, this compound may be introduced into cells through cellular membrane, may be localized in the mitochondria specifically and may be fixed onto the mitochondrial protein by forming a covalent bond.

In a neutral or a basic environment, fluorescent emission is quenched by a photo-induced electron transfer (PET) from a non-covalent electron pair of a nitrogen atom of an amine in a piperazine ring that does not conjugate with a π-electron system of a perylene ring to the π-electron system of the perylene ring, whereas on an acidic environment of which pH value is smaller than the pKa value of the amine that does not conjugate with π-electron system of the perylene ring, the π-electron system of the perylene ring emits fluorescence since no photo-induced electron transfer takes place because of a protonation of the nitrogen atom. Therefore, no fluorescent emission takes place when the mitochondria are in cytoplasm, whereas the fluorescent emission takes place in an "On-Off" manner when the mitochondria are engulfed in the lysosome in the process of mitophagy, that enables the mitochondria in the process of mitophagy to be distinguished by a fluorescence imaging.

Also, absorption wavelength and fluorescence wavelength of the pH responsive fluorescent compound represented by the general formula shown above are both longer than those of naphtahlimide etc., since it has the perylene imide as a fluorescent chromophore. Therefore, excitation by G excitation is also possible in addition to B excitation commonly used in the fluorescence microscope. That enables selective excitation in the presence of other organelle and other endogenous fluorescent substances, reduction of an influence of background emission or autofluorescence and detection of high sensitivity. In addition, since the pH responsive fluorescent compound represented by the general formula shown above has a wide π-conjugation plane, it also has a property of forming self-assembly in a polar solvent which leads to a concentration quenching. Therefore, the pH responsive fluorescent compound does not show fluorescent emission when it is dispersed in the cytoplasm, which makes the background emission lower.

By synergistically exhibiting these effects, the present disclosure provides a novel pH responsive fluorescent compound that may be localized to the mitochondria in the cells specifically, emits strong fluorescence in a slight acidic environment in the lysosomes and hardly affected by autofluorescence or background emission arised from other fluorescent substances in the cells, a composition for detecting the mitophagy using the same and a method for detecting the mitophagy within cells.

EMBODIMENT OF INVENTION

Figure 1:
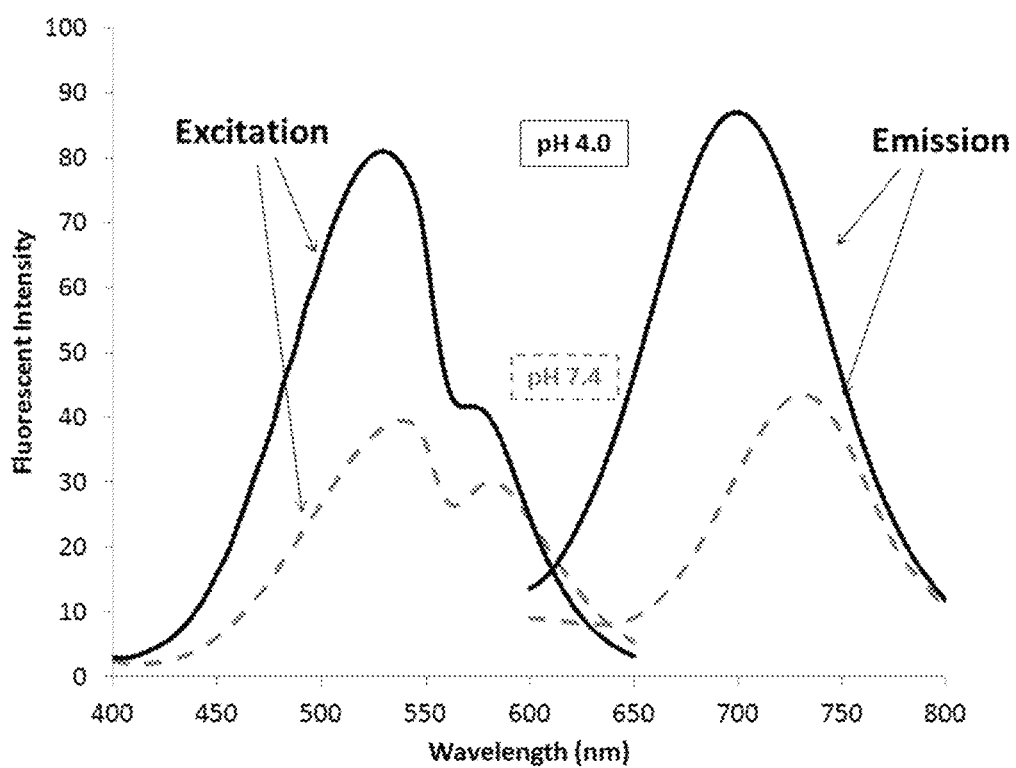
FIG. 1 shows absorption spectra and fluorescence spectra of a pH responsive fluorescent compound according to one embodiment of the present disclosure.

Specific embodiments of the present disclosure are described below to provide understanding of the present disclosure.

The pH responsive fluorescent compound according to the present disclosure is represented by a general formula shown below.

[Chemical Formula 4]

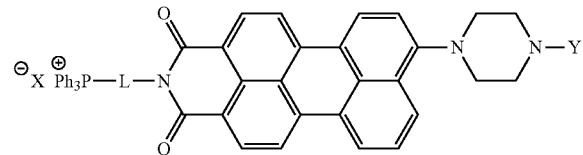

In the general formula as shown above,
L represents a linker;
X represents a pharmaceutically acceptable anion; and
Y represents a reactive group that may react with a functional group on a mitochondrial protein to form a covalent bond.

Linker (L)

As a linker (L) for linking perylene imide, a fluorescent chromophore and triphenyl phosphine group for specifically localizing into the mitochondria, any atomic group may be employed without limitation as long as it does not affect fluorescent emission properties of perylene imide group (for example, emission wavelength, emission intensity, pH-dependencies of emission intensity and excitation wavelength), localization to mitochondria, etc. A particular example of the linker L includes an alkylene group which may have oxygen atom, nitrogen atom, sulfur atom, ester linkage, amide linkage, urethane linkage, urea linkage (—NH—C(=O)—NH—), cycloalkylene group, arylene group or heteroarylene group, etc., between C—C bond or on a side chain and may also have one or more branches.

Anion (X)

As an anion X: a counter ion of triphenyl phosphonium group, pharmaceutically acceptable organic or inorganic anions may be employed without limitation as long as it does not affect fluorescent emission properties of perylene imide group (for example, emission wavelength, emission intensity, pH-dependencies of emission intensity and excitation wavelength), localization to mitochondria and reactivity with the mitochondrial proteins, etc., and it does not show cytotoxicity. A particular example of the anion X includes halide ions such as chloride ion and bromide ion; organic acid ions such as acetate ion, propionate ion, lactate ion, citrate ion and tartarate ion; inorganic acid ions such as nitrate ion and sulfate ion.

Reactive Functional Group (Y)

As a reactive functional group for reacting with a functional group on a mitochondrial protein to form a covalent bond, any functional group having an atom or an atomic group having appropriate reactivity such that it does not react with a cytosolic protein other than mitochondrial protein before localizing to mitochondria on one side and attached to a nitrogen atom on a piperazine ring may be employed without limitation as long as it does not affect fluorescent emission properties of perylene imide group (for example, emission wavelength, emission intensity, pH-dependencies of emission intensity and excitation wavelength), localization to mitochondria, etc. A particular example of the reactive functional group (Y) includes ω-chloroalkyl group, ω-bromoalkyl group and 4-chloromethylbenzyl group.

A preferable example of the pH responsive fluorescent compound is, for example a compound represented by Formula 9 shown below.

[Chemical Formula 5]

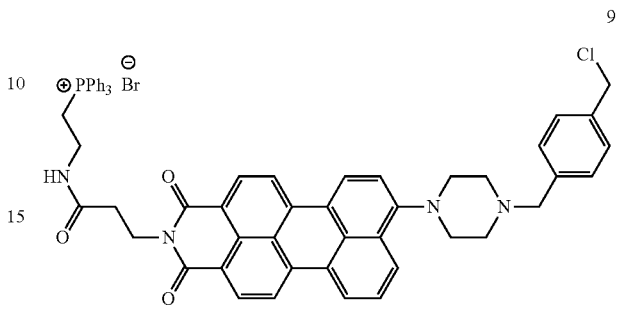

The compound represented by the general formula shown above may be synthesized by any synthetic routes (reactions and conditions) known in the art such as those shown in Examples below Since the compound represent by the general formula shown above (hereinafter it may be abbreviated to "the compound") has permeability to cell membrane, introduction of the compound to cells may be carried out by simply contacting the compound to the cell without using special technique. Thus, the mitophagy in cells may be detected by incubating the cells in which the compound has been introduced for certain period and measuring a fluorescent emission from the cells using any known means such as fluorescent microscopy. Certain embodiment of the present disclosure relates to a method for detecting mitophagy comprising a step for administering the pH responsive fluorescent compound represented by a general formula shown above into cells and a step for measuring a fluorescent emission from the cells after incubating for certain period.

The compound is used in the form of a solution or a dispersion in which the compound is dissolved or dispersed in an appropriate solvent of buffer in certain concentration to introduce into cells. Certain embodiment of the present disclosure relates to a composition in which the compound is dissolved or dispersed in an appropriate solvent of buffer in certain concentration.

EXAMPLES

Examples are provided below for confirmation of the effect of use of the present disclosure.

Example 1: Synthesis of the pH Responsive Fluorescent Compound

According to the scheme shown below, the pH responsive fluorescent compound represented by Formula 9 shown above (hereinafter, the pH responsive fluorescent compound represented by Formula n (n is an integer of 1 to 9) may abbreviated to "Compound n".) was synthesized.

[Chemical Formula 6]
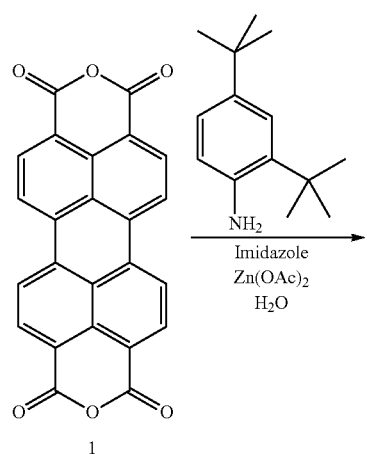
[Chemical Formula 7]
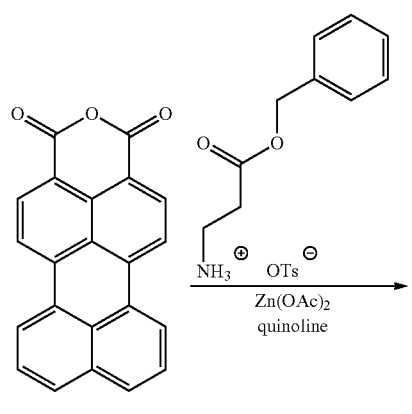

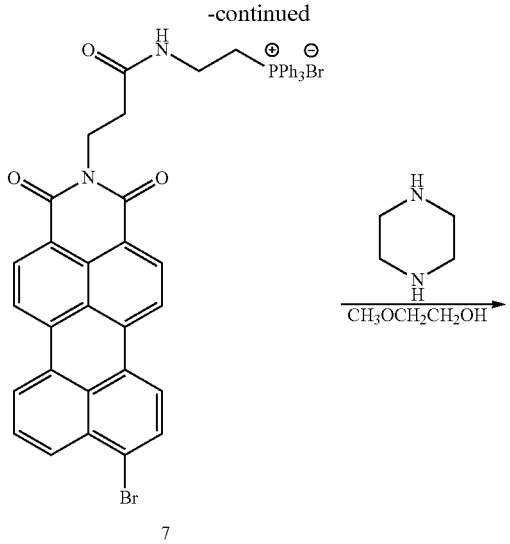

7

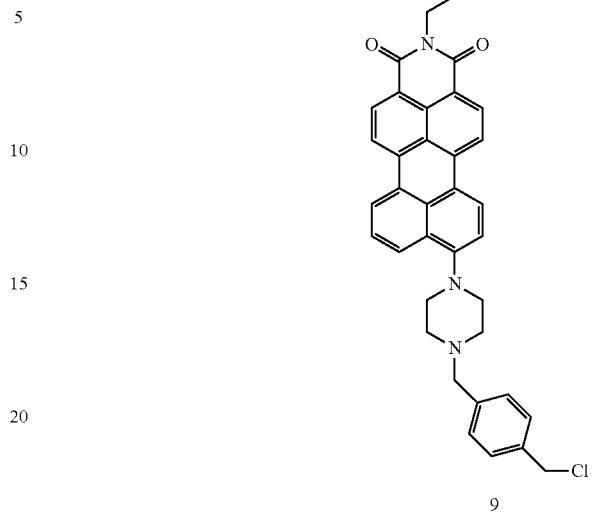

9

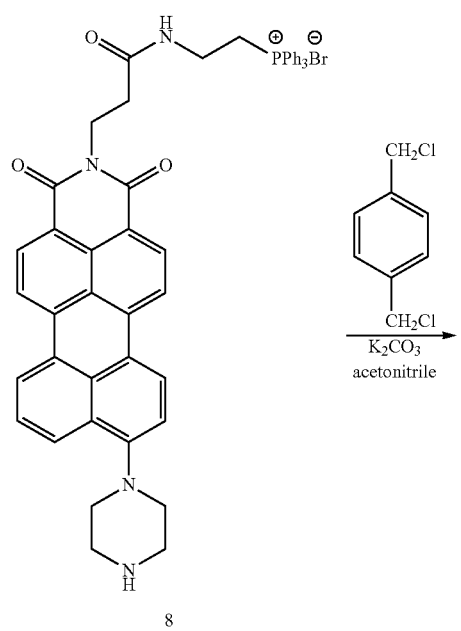

8

Synthesis of Compound 2

5.5 g (14 mmol) of Perylene-3,4,9,10-tetracarboxylic acid dianhydride (Compound 1), 1.57 g (7.6 mmol) of 2,5-di-tert-butyl aniline, 1.98 g (9.0 mmol) of zinc acetate dihydrate, 14 g (205.6 mmol) of imidazole and 12 mL of water were placed in a metal autoclave, well mixed with a spatula and reacted at 200° C. for 24 hours. After the reaction, contents were transferred to a 500 mL beaker and a residue was washed with about 200 mL of EtOH and poured into the beaker. To the mixture, 1 mL of concentrated hydrochloric acid was added dropwise, stirred for 1 hour at room temperature and EtOH was distilled off. $CHCl_3$ was added to the residue, the mixture was transferred to a separation funnel and washed with water 3 times. The $CHCl_3$ layer was dried over $Na_2SO_4$ and concentrated to dryness. The product was purified with column chromatography using chloroform/ethyl acetate 9:1 as an eluent (T, Dentani; et al., *Dyes Pigments.*, 2007, 72(3), 303-307.).

$^1$H-NMR (400 MHz, $CDCl_3$) δ:1.30 (s, 9H), 1.33 (s, 9H), 7.03 (s, 1H), 7.45 (d, 1H, J=8.4 Hz), 7.58-7.65 (m, 3H), 7.90 (d, 2H, J=7.9 Hz), 8.44 (m, 3H), 8.64 (d, 2H, J=7.8 Hz).

Synthesis of Compound 3

5 g (9 mmol) of Compound 2 was placed in a reaction vessel, dissolved with 10 mL of THF, to which 400 mL of i-BuOH was added. 36 g (645 mmol) of KOH flake was added and the mixture was refluxed at 110° C. for 2 hours. 400 mL of acetic acid was added dropwise and the mixture was stirred for 2 hours at room temperature. A black crystal precipitated was filtrated and dried in vacuo. Because of poor solubility of the compound thus obtained in organic solvents which hampered the NMR analysis, the product was used for next step without further purification.

Synthesis of Compound 4

1.5 g (4.5 mmol) of Compound 3, 1.86 g (5.3 mmol) of β-alanine benzyl ester p-toluene sulfonate, 795 mg (3.6 mmol) of zinc acetate and 150 mL of quinoline was added and the mixture was refluxed at 120° C. overnight in an argon atmosphere. $CHCl_3$ was added to the reaction mixture and washed with 3N HCl 3 times. The $CHCl_3$ layer was dried over $Na_2SO_4$ and concentrated to dryness. The product was purified with column chromatography using chloroform/ethyl acetate 9:1 as an eluent.

¹H-NMR (400 MHz, CDCl₃) δ:2.85 (t, 2H, J=7.2 Hz), 4.53 (t, 2H, J=7.2 Hz), 5.14 (s, 2H), 7.26-7.32 (m, 4H), 7.61 (t, 2H, J=7.6 Hz), 7.88 (d, 2H, J=8.0 Hz), 8.32 (d, 2H, J=7.4 Hz), 8.38 (d, 2H, J=7.1 Hz), 8.51 (d, 2H, J=8.0 Hz).

Synthesis of Compound 5

1.0 g (2.0 mmol) of Compound 4 was dissolved in a solvent mixture of 80 mL of THF and 20 mL of EtOH. A spatula tip (approximately 50 mg) of 10% Pd/C was added and the mixture was stirred at room temperature overnight in an H₂ atmosphere. Because of poor solubility of the compound thus obtained in organic solvents which hampered the NMR analysis, the product was used for next step without further purification.

Synthesis of Compound 6

Unpurified Compound 5 was dissolved in 250 mL of DMF. 981 mg (1.0 eq., 2.54 mmol) of (2-aminoethyl) triphenyl phosphonium bromide (synthesized according the method described in Maryanoff, B. E. et al., *J. Am. Chem. Soc.* 1985, 107, 217-226), 830 mg (1.2 eq., 3.05 mmol) of DMT-MM and 5 mL of DIEA was added and the mixture was stirred at room temperature overnight. After the progress of the reaction was monitored, the solvent was distilled by a rotary evaporator. The product was purified with column chromatography using chloroform/methanol 9:1 as an eluent.

¹H-NMR (400 MHz, CDCl₃) δ:2.65 (t, 2H, J=7.4 Hz), 3.73-3.81 (m, 2H), 3.86-3.93 (m, 2H), 4.40 (t, 2H, J=7.4 Hz), 7.56 (t, 2H, J=7.7 Hz), 7.69-7.86 (m, 15H), 8.20 (d, 2H, J=8.1 Hz), 8.29 (d, 2H, J=7.6 Hz), 8.38 (d, 2H, J=8.0 Hz), 8.80 (bt, 1H).

Synthesis of Compound 7

To 1.0 g of Compound 6, 150 mL of 1,2-dichloroethane and 539 mg (3.0 eq., 3.9 mmol) of K₂CO₃ was added and the mixture was stirred. 85 μL (2.5 eq., 3.28 mmol) of bromine diluted with 5 mL of 1,2-dichloroethane was added dropwise and the mixture was stirred at 100° C. for 2 hours. Progress of the reaction was monitored by an ESI-MS analysis. Since the polarity of brominated product was similar to that of the starting material, monitoring of the progress of the reaction by TLC was difficult. Since the result of the MS analysis showed that the peak of the starting material (m/z:761 [M+H⁺]) was not observed and the peak of the product (m/z:839 [M+H⁺]) was observed, the solvent was distilled by a rotary evaporator. The product was purified with column chromatography using chloroform/methanol 9:1 as an eluent.

¹H-NMR (400 MHz, CDCl₃) δ:2.65 (t, 2H, J=7.3 Hz), 2.79 (bs, 4H), 3.24 (bs, 4H), 3.68 (s, 2H), 3.72-3.77 (m, 2H), 3.83-3.88 (m, 2H), 4.41 (t, 2H, J=7.3 Hz), 4.6 (s, 2H), 7.66-7.86 (m, 17H), 8.13 (d, 1H, J=7.3 Hz), 8.25 (d, 2H, J=8.3 Hz), 8.29 (d, 1H, J=7.3 Hz), 8.38 (d, 1H, J=7.4 Hz), 8.43-8.48 (m, 2H), 9.19 (bt, 1H).

Synthesis of Compound 8

To 500 mg of Compound 7, 150 mL of 2-methoxyethanol and 3.5 g (66.6 eq., 40 mmol) of piperazine was added and the mixture was stirred at 140° C. overnight. After the progress of the reaction was monitored, the solvent was distilled by a rotary evaporator. The product was purified with column chromatography using chloroform/methanol 8:2 as an eluent.

¹H-NMR (400 MHz, CD₃OD) δ:2.56 (t, 2H, J=6.7 Hz), 3.15 (m, 1H), 3.50 (m, 1H), 3.52-3.63 (m, 4H), 4.40 (t, 2H, J=6.8 Hz), 7.20 (d, 1H, J=8.4 Hz), 7.58 (t, 1H, J=7.9 Hz), 7.74-7.93 (m, 15H), 8.09-8.19 (m, 5H, J=8.5 Hz), 8.30 (d, 1H, J=7.4 Hz), 8.36 (d, 1H).

Synthesis of Compound 9

300 mg of Compound 8, 1245 mg (20 eq., 7.1 mmol) of α,α'-dichloro-p-xylene and 50 mg (1.0 eq., 0.35 mmol) of K₂CO₃ was dissolved in 150 mL of acetonitrile and the mixture was refluxed overnight. Progress of the reaction was monitored by TLC. After the filtration, the reaction solution was distilled by a rotary evaporator to remove excess α,α'-dichloro-p-xylene. The product was purified with column chromatography using chloroform/methanol 9:1 as an eluent.

¹H-NMR (400 MHz, CDCl₃) δ:2.65 (t, 2H, J=7.3 Hz), 2.79 (bs, 4H), 3.24 (bs, 4H), 3.68 (s, 2H), 3.72-3.77 (m, 2H), 3.83-3.88 (m, 2H), 4.41 (t, 2H, J=7.3 Hz), 4.6 (s, 2H), 7.16 (d, 1H, J=7.3 Hz), 7.37-7.42 (m, 4H), 7.57 (t, 1H, J=7.9 Hz), 7.68-7.84 (m, 15H), 8.13-8.28 (m, 4H), 8.33-8.41 (m, 3H), 9.19 (bt, 1H).

Compound 9 has perylene imide as a fluorescent chromophore. Since a maximum excitation wavelength of perylene imide is 530 nm, it is a fluorescent molecule that is compatible with widely used laser microscope and may be detected with high sensitivity. In addition, because of its longer excitation wavelength, excitation of endogenous fluorescent substances in cells may be avoided, by which one can expect that background emission is lowered. The compound also has a piperazine ring having a pH sensor functionality; a triphenyl phosphonium group for specifically localizing into the mitochondria; and a chlorobenzyl group as a fixation group. The characteristic of the compound is that their fluorescent intensity is low in a pH environment in the vicinity of mitochondria, whereas their fluorescent intensity is high in a weakly acidic environment in lysosomes based on a quenching by a photo-induced electron transfer (PET) from the piperazine ring to the perylene imide group. In addition, the compound is introduced and localized into intracellular mitochondria by the triphenyl phosphonium group in a membrane potential dependent manner and fixed onto the mitochondria via a covalent bond formed by a reaction of the chlorobenzyl group and the functional group of the mitochondrial protein (for example, SH group in a cysteine residue).

Example 2: Fluorescent Property of Compound 9

It was found that Compound 9 tends to form a self-aggregate in a polar solvent which leads to a decrease of fluorescent intensity because of its wide conjugation plane. In other words, an imaging of high sensitivity with low background emission may be expected since Compound 9 diffused in cytoplasm shows no fluorescent emission. To investigate a pH-dependent fluorescent emission of Compound 9, excitation spectra ("Excitation" in FIG. 1) and fluorescence spectra ("Fluorescence" in FIG. 1) were measured at pH 4.0 and 7.4 in buffer solution containing 50% acetonitrile. The excitation spectra and the fluorescence spectra thus obtained are shown in FIG. 1. As evident from FIG. 1, Compound 9 shows large Stokes shift. It is also shown that the fluorescent intensity at pH 4.0 is higher than that at pH 7.4 and the maximum fluorescent wavelength shifts to short-wavelength side by 30 nm.

Figure 2:
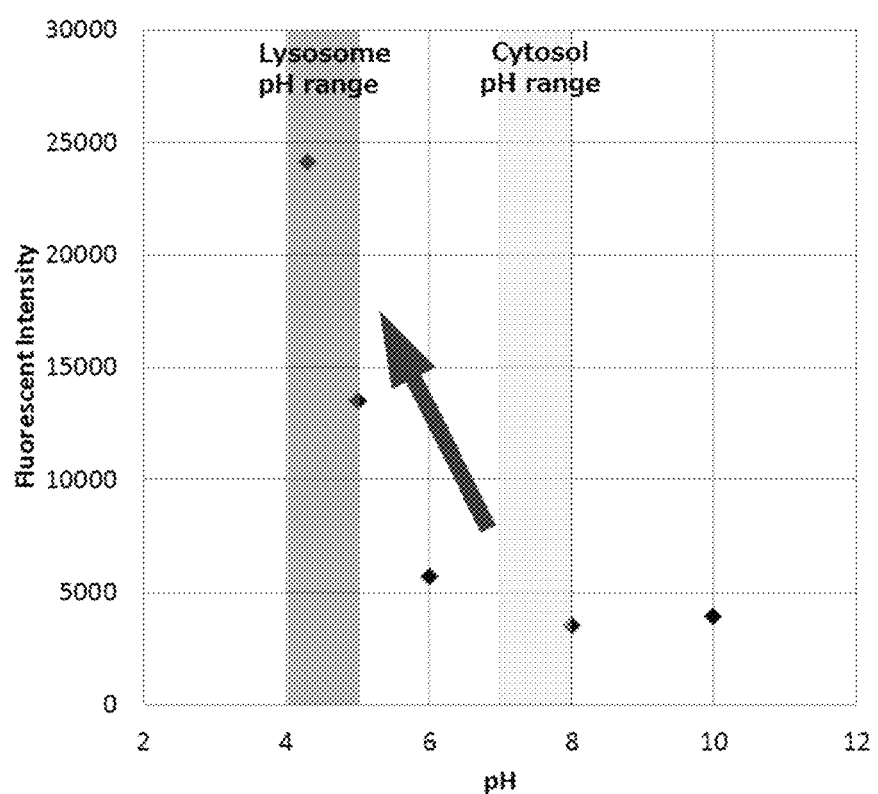
FIG. 2 shows a graph illustrating a change of fluorescent intensity of the pH responsive fluorescent compound responding to pH change.

The fluorescent intensities of Compound 9 at various pH were measured in buffer solution containing 50% DMSO. The results are shown in FIG. 2. It is shown that the fluorescent intensity of Compound 9 increases from a neutral region to an acidic region. Such increase takes place at more acidic side than that of naphthyl imide-type pH-responsive fluorescent compound. Hence, one can expect that Compound 9 is a fluorescent dye hardly affected by other organelles in cells.

Example 3: Mitophagy Detection Test Using HeLa Cells (1)

Figure 3:
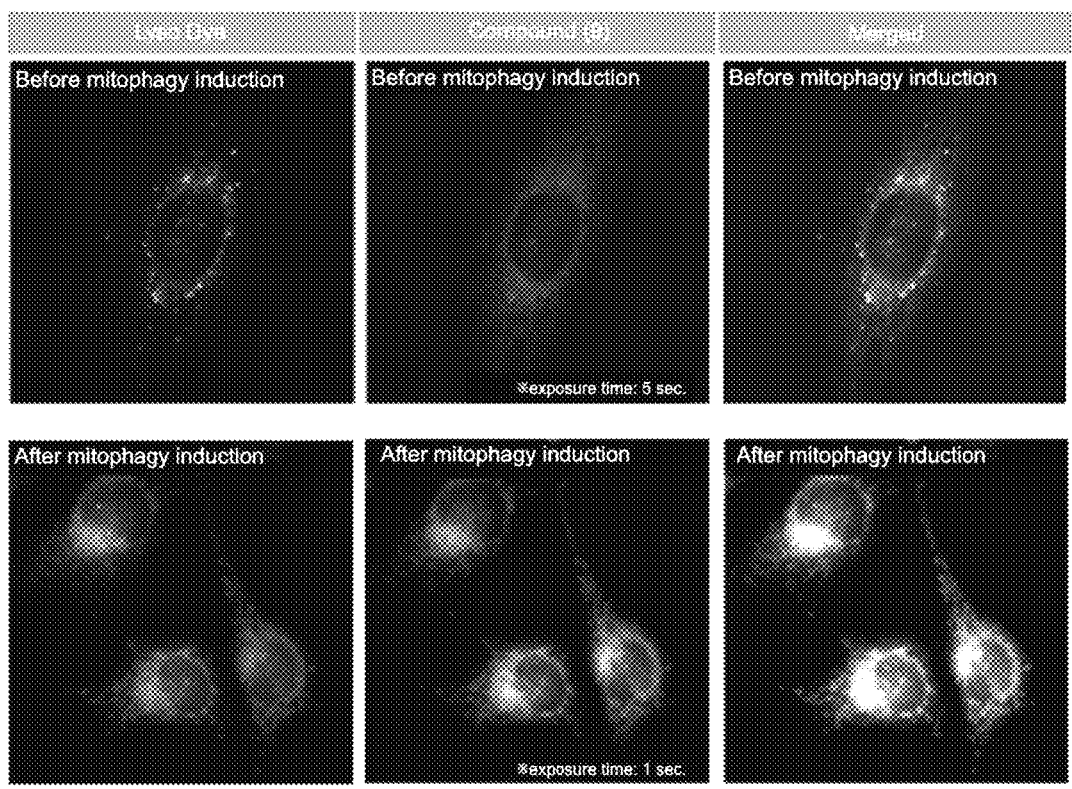
FIG. 3 shows fluorescent microscopic images of HeLa cells in which the pH responsive fluorescent compound is introduced before and after inducing mitophagy.

HeLa cells were seeded on a μ-slide 8 well (Ibidi) and incubated in a $CO_2$ incubator at 37° C. overnight. Compound 9 diluted with Hanks' HEPES buffer (100 nmol/L) was added and incubated for 30 minutes. A starvation induction was carried out by washing cultured cells with Hanks' HEPES buffer twice follow by adding plasma-free Krebs' buffer containing 1 μM glucagon and 7.5 μM pepstatin A and incubating at 37° C. for appropriate period. Then, the cultured cells were observed by a fluorescent microscope. The results of the observation of HeLa cells before and after inducing mitophagy are shown in FIG. 3. To confirm the uptake of Compound 9 in lysosomes, 1 μM Lyso Dye diluted with Hanks' HEPES buffer was added to the cultured cells and incubated at 37° C. for 30 minutes. After washing with Hanks' HEPES buffer twice, the fluorescent microscopic measurement showed that collateral stain took place.

Example 4: Mitophagy Detection Test Using HeLa Cells (2)

Methods for inducing mitophagy include, in addition to a bulk method such as described in Example 3 above, a selective method mediated with Parkin gene and PINK1 enzyme. The latter involves Parkinson disease and the relationship with a quality control of dysfunctional mitochondria (For example, see Derek Narendra, Atsushi Tanaka, Der-Fen Suen and Richard J. Youle, *J. Cell Biol.*, 2008, 183, 795-803.). To examine the mitochondria-selective detection of autophagy, Parkin-expressed HeLa cells were prepared and the mitophagy was induced by adding Compound 9 and carbonyl cyanide m-chlorophenyl hydrazone (CCCP), a mitochondrial uncoupler and incubating.

<Confocal Laser Microscopic Detection Using Parkin-Expressed HeLa Cells>

HeLa cells were seeded on a μ-slide 8 well (Ibidi) and incubated in a $CO_2$ incubator at 37° C. overnight. Parkin plasmid was introduced using HilyMax (DOJINDO LABORATORIES) into the cells and the cells were incubated overnight. The cultured cells were washed with a plasma-containing medium, to which Compound 9 diluted with Hanks' HEPES buffer (100 nmol/L) was added and incubated for 30 minutes. After washing with the plasma-containing medium, the cells were cultured in a cell culture medium containing 10 μM/L of CCCP for 24 hours. After the occurrence of mitophagy was monitored by the fluorescent microscope, the cultured cells were further incubated with 1 μM Lyso Dye at 37° C. for 30 minutes. After washing with hanks' HEPES buffer twice, the fluorescent microscopic measurement showed that collateral stain took place.

Figure 4:
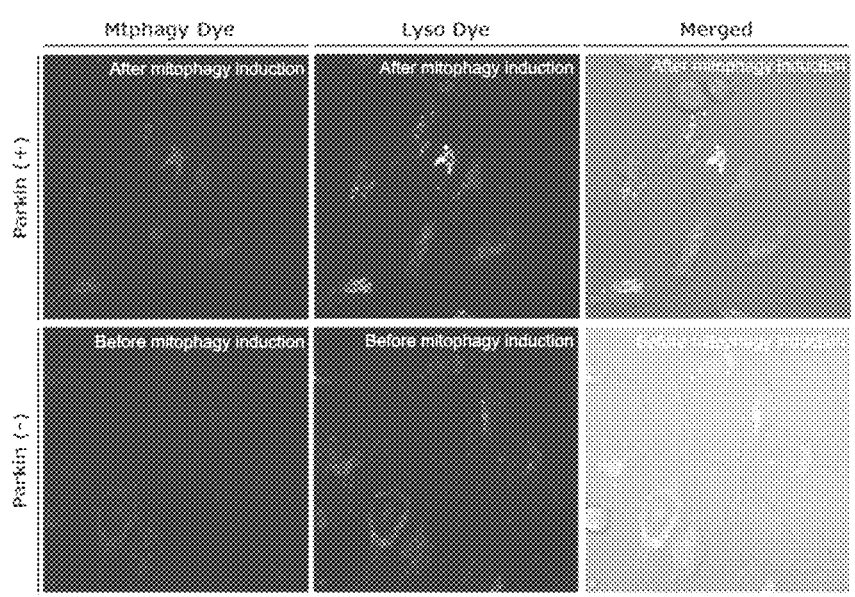
FIG. 4 shows fluorescent microscopic images of Parkin-expressed HeLa cells and Parkin-non-expressed HeLa cells in which the pH responsive fluorescent compound is introduced.

The fluorescence images taken by the confocal laser microscope (see FIG. 4) show that the fluorescence from Compound 9 in Parkin-non-expressed HeLa cells (parkin (−)) observed is faint. On the contrary, in the Parkin-expressed HeLa cells (parkin(+)), the fluorescence form Compound 9 is observed as well as the collateral stain with a lysosome dye (Lyso Dye) is observed (see FIG. 4), which shows that mitochondria is enveloped with lysosomes and Compound 9 is a dye which may detect mitophagy under the condition in which mitochondria-selective autophagy is induced.

<Flow Cytometry (FCM) Analysis Using Parkin-Expressed HeLa Cells>

HeLa cells were seeded on a 24 well plate and incubated in a $CO_2$ incubator at 37° C. overnight. Parkin plasmid was introduced using HilyMax (DOJINDO LABORATORIES) into the cells and the cells were further incubated overnight. The cultured cells were washed with a plasma-containing medium, to which Compound 9 diluted with Hanks' HEPES buffer (100 nmol/L) was added and incubated for 30 minutes. After washing with the plasma-containing medium, the cells were cultured in a cell culture medium containing 10 μM/L of CCCP for 24 hours. After washing with PBS, the cells were peeled off by trypsin and EDTA. The cells were collected by centrifuge, dispersed in 0.5 mL of HBSS and analyzed by FCM (BD FACS cant II).

Figure 5:
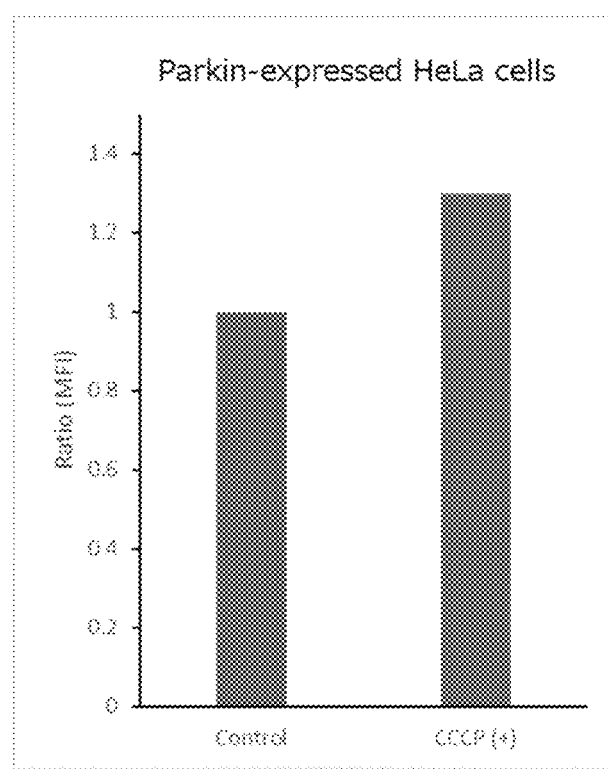
FIG. 5 shows a graph illustrating results of flow cytometry measurement of Parkin-expressed HeLa cells and Parkin-non-expressed HeLa cells.

The result of quantitative analysis using flow cytometry (FCM) showed that induction of mitophagy using CCCP lead to an increasing of fluorescent emission by 1.3 times (see FIG. 5). These results show that Compound 9 is a fluorescent dye capable of detecting mitophagy using a fluorescence imaging and FCM.

The invention claimed is:

1. A pH responsive fluorescent compound represented by Formula 9 as shown below:

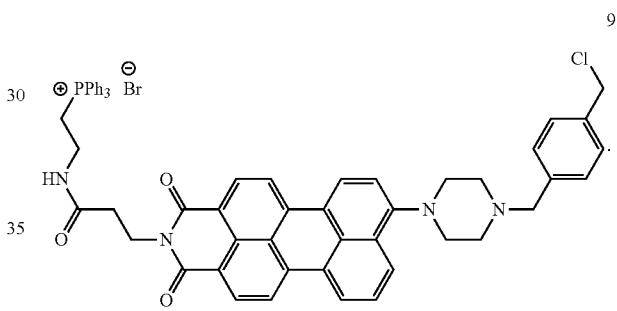

2. A composition for detecting mitophagy containing a pH responsive fluorescent compound represented by Formula 9 as shown below:

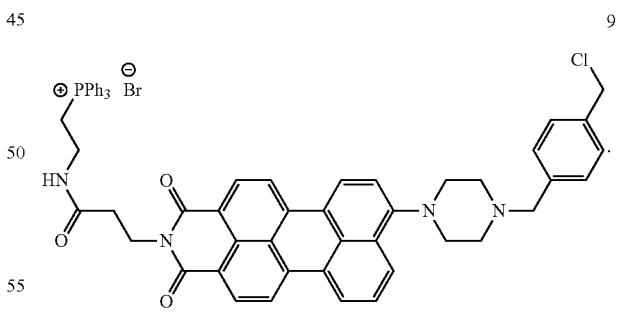

3. A method for detecting mitophagy comprising:
   a step for administering a pH responsive fluorescent compound represented by Formula 9 as shown below into cells;
   a step for localizing the RI-1 responsive fluorescent compound in mitochondria; and
   a step for monitoring mitophagy by measuring a fluorescent emission from the cells arising from an uptake of the mitochondria into lysosome after incubating for certain period;

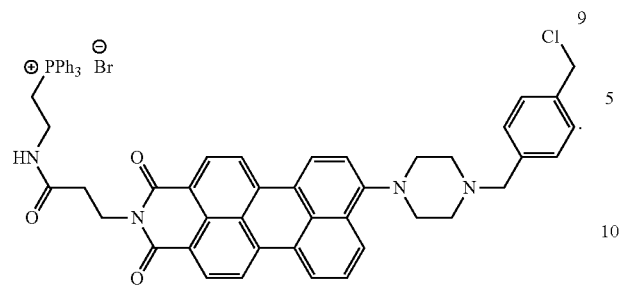
* * * * *